(12) United States Patent
Mason et al.

(10) Patent No.: US 10,702,688 B2
(45) Date of Patent: Jul. 7, 2020

(54) VASCULAR ACCESS DEVICE

(71) Applicant: ACCESS FOR LIFE INC., Fleetwood, NY (US)

(72) Inventors: Roger A. Mason, Blytheville, AR (US); Philip Libman, ShaArei Tikva (IL)

(73) Assignee: Access for Life Inc., Fleetwood, NY (US)

(*) Notice: Subject to any disclaimer, the term of this patent is extended or adjusted under 35 U.S.C. 154(b) by 41 days.

(21) Appl. No.: 15/569,392

(22) PCT Filed: May 11, 2016

(86) PCT No.: PCT/US2016/031771
§ 371 (c)(1),
(2) Date: Oct. 26, 2017

(87) PCT Pub. No.: WO2016/183145
PCT Pub. Date: Nov. 17, 2016

(65) Prior Publication Data
US 2018/0289939 A1  Oct. 11, 2018

Related U.S. Application Data

(60) Provisional application No. 62/159,616, filed on May 11, 2015.

(51) Int. Cl.
*A61M 39/02* (2006.01)
*A61M 1/36* (2006.01)

(52) U.S. Cl.
CPC .... *A61M 39/0247* (2013.01); *A61M 39/0208* (2013.01); *A61M 1/3655* (2013.01);
(Continued)

(58) Field of Classification Search
CPC ...... A61M 39/0247; A61M 2039/0202; A61M 2039/0205; A61M 2039/0258;
(Continued)

(56) References Cited

U.S. PATENT DOCUMENTS 4,164,221 A * 8/1979 Bentley ............ A61M 39/0247
251/291
4,318,401 A * 3/1982 Zimmerman ...... A61B 17/3415
604/165.01
(Continued)

FOREIGN PATENT DOCUMENTS

| WO | WO 2010/124057 | 10/2010 |
| WO | WO 2014/020565 | 2/2014 |
| WO | WO 2016/183145 | 11/2016 |

OTHER PUBLICATIONS

International Preliminary Report on Patentability dated Nov. 17, 2017 From the International Bureau of WIPO Re. Application No. PCT/US2016/031771. (9 Pages).
(Continued)

*Primary Examiner* — Kami A Bosworth

(57) ABSTRACT

A system and method are provided for vascular access, enabling repetitive vascular access while preventing damage to the blood vessel wall, reducing hematomas, improving flow in a vessel, preventing back-wall perforation, and enabling improved fistula maturation and care. The system includes an implanted conduit that is incorporated into surrounding fibrous tissue that can guide a needle and/or catheter from a puncture site on the skin to a vessel wall, which may be used to provide repetitive vascular access for persons requiring hemodialysis or chemotherapy.

26 Claims, 14 Drawing Sheets

(52) U.S. Cl.
CPC ............... *A61M 2039/027* (2013.01); *A61M 2039/0258* (2013.01); *A61M 2039/0261* (2013.01); *A61M 2039/0273* (2013.01); *A61M 2039/0276* (2013.01); *A61M 2039/0282* (2013.01); *A61M 2205/582* (2013.01); *A61M 2206/11* (2013.01)

(58) Field of Classification Search
CPC .. A61M 2039/0261; A61M 2039/0264; A61M 2039/027; A61M 2039/0273; A61M 2039/0276; A61M 2039/2079; A61M 2039/0291; A61B 17/3423; A61B 2017/3425
See application file for complete search history.

(56) References Cited

U.S. PATENT DOCUMENTS

| | | | | |
|---|---|---|---|---|
| 5,085,646 | A * | 2/1992 | Svenson | A61M 39/0247 604/175 |
| 5,281,199 | A | 1/1994 | Ensminger et al. | |
| 5,728,103 | A * | 3/1998 | Picha | A61B 17/3423 604/174 |
| 5,807,356 | A | 9/1998 | Finch, Jr. et al. | |
| 5,911,706 | A | 6/1999 | Estabrook et al. | |
| 6,004,301 | A * | 12/1999 | Carter | A61M 39/0247 604/256 |
| 6,007,576 | A * | 12/1999 | McClellan | A61F 2/064 623/23.64 |
| 6,099,508 | A | 8/2000 | Bousquet | |
| 6,398,764 | B1 | 6/2002 | Finch, Jr. et al. | |
| 7,922,733 | B2 | 4/2011 | Borghi | |
| 2004/0243064 | A1* | 12/2004 | Sommerich | A61M 39/0247 604/175 |
| 2005/0171565 | A1 | 8/2005 | Yencho et al. | |
| 2007/0065481 | A1 | 3/2007 | Chudzik et al. | |
| 2008/0171961 | A1* | 7/2008 | Lane | A61M 1/3621 604/4.01 |
| 2008/0249509 | A1* | 10/2008 | Glenn | A61M 39/0208 604/539 |
| 2009/0131919 | A1* | 5/2009 | Davey | A61M 25/04 604/891.1 |
| 2009/0171295 | A1* | 7/2009 | Porter | A61F 2/0077 604/175 |
| 2010/0191166 | A1* | 7/2010 | Phillips | A61B 17/0057 604/6.16 |
| 2010/0274223 | A1* | 10/2010 | Teitelbaum | A61B 17/064 604/507 |
| 2012/0245536 | A1* | 9/2012 | Gerber | A61M 39/0208 604/288.02 |
| 2013/0245572 | A1 | 9/2013 | Young et al. | |
| 2014/0039249 | A1 | 2/2014 | Atalla | |

OTHER PUBLICATIONS

International Search Report and the Written Opinion dated Aug. 16, 2016 From the International Searching Authority Re. Application No. PCT/US2016/031771. (11 Pages).

* cited by examiner

VASCULAR ACCESS DEVICE

CROSS REFERENCE TO RELATED APPLICATIONS

This application claims the benefit of U.S. Provisional Application No. 62/159,616, filed May 11, 2015, which is incorporated by reference.

FIELD OF THE INVENTION

The invention is related to a subcutaneously implanted vascular access device that facilitates access to the vascular system.

BACKGROUND OF THE INVENTION

Repetitive, secure access to a blood vessel is often required by patients with chronic diseases. A subset of these patients, dialysis patients, require access to a high flow vessel.

For example, end stage renal failure patients need repeated, chronic access to the vascular system to allow life sustaining hemodialysis. In the United States, an estimated 421,349 patients per year undergo hemodialysis and, thus, require maintenance of a vascular access site. The annual estimated cost associated for dialysis patients is approximately $73,000 dollars and a significant portion of these costs is spent on maintaining vascular access capability. Cumulatively, $30.9 billion U.S. dollars/year are spent, equal to approximately 7.1 percent of the Center for Medicaid and Medicare Services total budget (United States Renal Data System 2015 USRDS annual data report: Epidemiology of Kidney Disease in the United States. National Institutes of Health, National Institute of Diabetes and Digestive and Kidney Diseases, Bethesda, Md., 2015).

Repetitive puncture of a blood vessel in a localized area may ultimately lead to weakening of the vessel wall in that area that can result in aneurysm formation (a ballooning out of the vessel wall) which may eventually rupture with serious bleeding. A blood clot may also form within the aneurysm that can ultimately cause a thrombosis (blood clot) of the fistula.

Furthermore, repetitive needle punctures of a blood vessel may result in damage to the vessel wall causing scar tissue formation, narrowing the vessel (stenosis), and causing it to be nonfunctional.

Another complication of repetitive punctures is hematoma formation. This may be caused by back wall vessel perforation by a needle after penetrating the front wall, or upon needle extraction from the front wall, if inadequate pressure is applied to the blood vessel to allow sealing of the puncture hole with a blood clot.

Still further complications may occur if, after extraction of the needle from the blood vessel, excessive pressure is applied to the vessel to avoid leakage from the puncture hole. The excessive pressure may shut off blood flow in the vessel, resulting in a complete clotting of the vessel.

Currently, there are three commonly used systems to establish vascular access for kidney failure patients: catheter-based access, native arterial venous fistula, and synthetic graft fistula. All techniques commonly have complications that require interventions to reestablish access.

Catheter-based access. This system may include a synthetic catheter that is placed transcutaneously, allowing the dialysis technician to attach the patient's catheter to the hemodialysis machine. Although this system offers immediate availability for use after placement, there may be several disadvantages. First, the system may be prone to infection, particularly for transcutaneously placed catheters where infection can develop at the skin exit site due to inadvertent breaks in the sterile technique by technicians. The presence of a foreign body in the vascular system is prone to seeding from distant sources of infection in the patient via the bloodstream. When a catheter becomes infected, removal is usually required to clear the infection. As a result, another catheter must be placed at another site to resume treatment. This requirement results in the additional cost and inconvenience of performing an additional surgical procedure as well as the cost of the replacement catheter.

Second, the relatively small caliber of the synthetic tubes placed in the vascular system may permit only limited blood flow through the system while a patient is on the dialysis machine. This may prolong the time each patient needs to be dialyzed and may indirectly contribute to the frequency of dialysis treatments.

Third, the catheter system introduces a foreign body in a central vein. This can lead to further complications including, for example, frequent formation of fibrin clots or blood clots in the lumen of the tube requiring the infusion of costly thrombolytic drugs to clear the catheter. Sometimes even more costly endovascular procedures are required to reestablish function in a catheter. Furthermore, the foreign body in the vascular system may result in a thrombosis or a narrowing (stenosis) of a major vein (subclavian vein or superior vena cava) that then precludes using that vein for future venous access in that patient. This complication can have life threatening ramifications particularly if the stenosis involves the superior vena cava.

Native Arterial Venous Fistula. A second mode of vascular access requires the construction of a connection between a patient's native vein and an adjacent artery (an Arterial Venous (AV) fistula), that creates a high flow of blood through a limited portion (generally 15-20 cm) of the patient's vascular system. This superficially positioned native vascular conduit usually grows to a certain minimal size (approximately 5-6 mm or greater in diameter) that then provides a target for the dialysis technician to insert the two needles that are required to place a patient on the dialysis machine. Some advantages of a native AV fistula may include, for example, longevity, immunity from infection, and low cost. This type of fistula has the longest life span of all known types of vascular access, lasting from several years up to twenty years or more, with the possibility of performing a secondary surgical intervention to salvage the functioning of the fistula even if complications do develop with the fistula over time. Also, since the fistula is constructed of native tissue, it is relatively immune to infection. Moreover, the fistula is cheaper to construct since there is no requirement for a costly catheter or synthetic graft.

On the other hand, since there are limited sites for the creation of a functioning fistula in each patient, the current standard of care is to perform the fistula in the most distal vessels in a patient's upper extremity where a preoperative assessment indicates that the fistula has a reasonable chance for maturing successfully. A 20% failure rate is considered acceptable for first time fistulas as vascular access surgeons try to maximize the available sites in a patient, cognizant that patients may require new fistulas at other sites in the future if the primary fistula eventually fails. This 20% failure rate can lead to further operations and, thus, significant additional costs and inconvenience to the patient.

Synthetic Graft Fistula. A third mode of vascular access requires the placement of a synthetic graft in a subcutaneous position, usually in a patient's upper extremity. The technician achieves access to the vascular system by placing needles directly into the easily palpable graft. Some advantages may include that the graft provides a reliable, easily accessible conduit to access to connect a patient to the dialysis machine. This choice of access is particularly valuable in patients who do not have the requisite minimally sized vein that will permit the establishment of a native AV fistula.

On the other hand, the cost of such a graft is approximately $3,292 (US) per patient. Also, the most commonly placed grafts require several days and up to several weeks for perioperative swelling to decrease and for the grafts to become sufficiently incorporated into a patient's tissues to allow safe access via the graft. The graft can also become infected by inadvertent lapses of sterile technique by the dialysis technician or through seeding from distant sources in the patient. An infected graft frequently requires a very costly and inconvenient (to the patient) series of procedures that includes removal of the infected graft, placement of an interim dialysis catheter, and a subsequent implantation of a new graft after the infection has been definitively treated to reestablish vascular access. A synthetic graft can also be prone to development of early or late thrombosis due to its synthetic, foreign quality.

Moreover, the site of the venous anastomosis between the graft and the patient's native vein can be a frequent site of stenosis that develops from a mismatch in the distensibility characteristics of the patient's native vein and the synthetic graft. This can require secondary costly surgical or endovascular interventions to correct the problem and to preserve continued functioning of the graft as a viable access conduit. Some grafts may even form a stenosis within the graft due to a proliferation of fibrin and scar tissue that requires a secondary procedure to maintain the viability of the graft. Additionally, repeated puncture of a graft in the same location by the dialysis technician can lead to a pseudoaneurysm formation (i.e., a localized collection of blood) that can eventually lead to failure of the graft if not corrected. Improper technique by the dialysis technician can also result in a hematoma formation during access to the graft or following removal of the needles at the end of the dialysis run. The hematoma may make access to the graft in that location difficult or impossible for a period of time, and may lead to occlusion of the graft.

Methods of vascular access that require fistula access are highly dependent on the skill of the dialysis technician. A fistula that, at maturation, is somewhat smaller than desirable, or is located deeper in the patient's tissues thereby presenting a less easily palpable target than normal, is more likely to be damaged during attempts to access the fistula. In the United States, the preferred method that is taught to access native fistulas is the step ladder approach, i.e., constantly moving the locations where the two access needles are placed in the fistula. The protocol of sticking needles into the fistula at different locations at each dialysis session leads to increased pain experienced by the patient since the effect of a localized area of insensitive scar tissue—e.g., where the fistula is accessed using the buttonhole technique (discussed further below)—is never allowed to form. Moreover, the native fistula may require at least 6 weeks and sometimes up to several months to mature, i.e., to grow to an adequate size and increased thickness of its walls that will allow the vessel to be safely punctured with a needle. During the maturation time for a fistula, a bridging dialysis catheter must be placed in the patient's central venous system to allow a patient to be dialyzed. Thus, there exists a need for a vascular access device that is capable of being used prior to fistula maturation.

Another approach, the buttonhole technique to access fistulas, has been shown in some studies to increase the longevity of a fistula while decreasing complications associated with moving access sites to different locations in the fistula during subsequent dialysis sessions. Some advantages of the buttonhole technique may include: (a) two nearby needle puncture points to access the fistula (approximately 3 cm apart) require only a relatively short functioning and accessible fistula to access the bloodstream; (b) blunt needle access through a fistulous opening in the skin into a scar tissue cylindrical track that leads the needle down to and into the vessel causes less patient discomfort (c) the narrow cicatricial cylindrical tract self-seals relatively easily with thrombus after removal of the needles following a dialysis run, eliminating the incidence of perifistula hematomas on the front wall of the fistula that can temporarily, or even permanently, incapacitate a fistula; and (d) after a cicatricial track has been established, blunt needles can be used to access the graft, decreasing the incidence of needle point damage to the back wall of the fistula when inserting needles.

A disadvantage of the buttonhole approach is that it requires a highly skilled dialysis technician to create a button-hole track. Ideally, a single, highly-skilled technician will repetitively perform the needle insertion on the same patient during the initial dialysis sessions, following the exact needle track in the same patient (same entrance point, same angle, same depth) every time for the first 10-15 access events until a well formed tract has developed. The logistical difficulty of having the same highly-skilled technician available for the first 10-15 access events in an individual patient currently limits the wider applicability of this technique.

U.S. Pat. No. 8,414,530, to Roger Alan Mason, herein incorporated by reference in its entirety, teaches the use of a vertically oriented chamber which guides a needle to a site in a blood vessel. Improvements to this device have been made which are incorporated into the present disclosure.

Vascular access devices that substantially overcome the foregoing disadvantages are needed.

SUMMARY OF THE INVENTION

One object of the invention is to provide a fibrous conduit from the skin to a blood vessel or graft in a patient undergoing dialysis, or the like, such as will facilitate repeated access to the vessel. The conduit affords advantages of the buttonhole technique for repeated vascular access, but requires less skill on the part of the professional puncturing the vessel wall.

Thus, the present invention is drawn to a device and method of vascular access that guides a needle from the skin into an opening in a vessel. In an embodiment of the invention, the opening will be the exact same opening in the vessel every time the vessel is accessed.

The vascular access device of the present invention may be used to treat a person who requires safe vascular access, including, but not limited to, those persons requiring hemodialysis or chemotherapy. The vascular access device may provide safer repetitive access to a blood vessel. A "vessel", as used herein, includes any conduit that blood flows in, for example, but not limited to, a native AV fistula, an AV fistula synthetic graft, a vein, or an artery.

An important feature of the device is that no portion of the device resides within the blood vessel. Previously existing vascular access devices describe components that enter the blood vessel lumen or that disrupt the interior lining of the vessel. Permanent indwelling components of vascular access devices are prone to infection, can cause vessel stenosis, (narrowing) and thrombosis (clotting). The present device eliminates these complications since the device is attached to the outside of the wall of the vessel, and it relies on the interior geometric configuration of the device to guide a needle to puncture the vessel wall at the same location every time.

Whereas the prior art in some instances has described a conduit or chamber that guides a needle or catheter to a site on a blood vessel, clinicians have found that the opening of the conduit may be difficult to locate, particularly when the opening is relatively deep in the tissue. The conduit according to embodiments of the present invention may be provided with a cylindrical shape with multiple pores, similar in design to a conventional arterial stent, except that instead of being placed in an artery, the device according to the invention is adapted to be placed between a blood vessel and the skin, traversing the subcutaneous fatty tissue, and designed to encourage ingrowth of fibrous tissue to incorporate the device in native tissues and therefore decreasing its vulnerability to infection. In the process, it is intended to form a fibrous track, extending from the skin to the vessel, completely replicating, by the use of a device, the end result of the traditional buttonhole technique which causes the creation of a scar tissue track from the skin to the vessel, but which is highly dependent on the experience of a highly skilled dialysis technician to create.

Additionally, in the prior art, and in the buttonhole technique, the vessel might be inadvertently harmed by a technician who perforates the back wall of the vessel when he/she advances the needle too far into the vessel. A novel design improvement in the current device includes a bump or stopper as a protuberance, or a tilting disk, built into the interior lumen of the device which prevents a needle from being advanced too far into the vessel and potentially endangering the vessel with a back wall perforation.

In addition, there is a novel design feature in the cylinder to prevent back bleeding into the device using either a one way valve at the distal end of the cylinder just before the needle penetrates the vessel, or other means, such as a catheter with a balloon on the outside of the catheter which may be inflated after the catheter is withdrawn into the cylinder, at the end of dialysis, which will cause a thrombus to form in the distal cylinder preventing back bleeding into the cylinder.

In embodiments, the vascular access device comprises a main body with a first end at or just below the skin and a second end that is contiguous with a vessel. In this context, just below the skin may mean up to about 3 mm, but may vary depending on the patient. The main body may have an inner surface defining a lumen that extends from the first end to the second end along an axis which forms an angle with the axis of the vessel of less than 45 degrees, and preferably in a range of approximately 5 degrees up to 30 degrees. The low angle of entry to the vessel results in better flow dynamics in the vessel, distal to the place where the needle punctures the vessel. This is expected to reduce turbulence inside the vessel.

The vascular access device may include a septum or a valve, at the first end of the vascular access device that acts as a self-sealing hemostatic barrier. There may also be a self-sealing membrane between the first end where the needle enters and the second end where the device is attached to the vessel wall. The vascular access device may also include a fluid sealed central cavity that may include an anticoagulant to prevent blood clots inside the cavity. The vascular access device may also include a one-way valve at the second (distal) end of the cavity which the needle traverses just prior to entering the blood vessel, with the valve preventing back bleeding into the main body. In an embodiment of the invention, a vascular access device may have a footplate for the device that is configured for attachment to the wall of a vessel. The footplate may be comprised of a polymer or metal or may comprise a synthetic mesh material with the mesh promoting tissue growth into the patch and simultaneously affixing the vascular access device to the blood vessel. The vascular access device may comprise one or more apertures on the fore and aft sides of its footplate, to affix the vascular access device to the vessel wall using sutures. There may be one or more wings containing apertures on either side of the superior aspect of the main body of the vascular access device which contain holes to enable suture fixation of the vascular access device to the surrounding subcutaneous tissue to prevent rotation of the vascular access device on the vessel.

In embodiments, a device according to the invention may be adapted to prevent blackflow without providing a valve by using an inflatable balloon on a catheter. Assuming a blunt needle is advanced in the cylinder to a stop approximately 5 mm from the end of the cylinder leading from the skin to the vessel, a plastic catheter is then advanced approx. 2 cm. or more beyond the tip of the blunt needle entering the vessel for approximately 1.5 cm or more. After dialysis, the catheter is withdrawn until it is entirely within the cylinder. A balloon, on the outside of the catheter but circumferentially around the catheter is inflated (by the technician who uses an accessory separate channel adjacent to the main channel on the catheter that is accessible on the end of the catheter coming through the skin. The syringe will contain a prepackaged measured amount of saline so the balloon cannot be overinflated. The balloon is left inflated for five minutes and then deflated once a clot has formed distal to the balloon in the end of the cylinder (replicating the formation of a clot in the end of the buttonhole track that forms when the technician puts pressure for 5-10 minutes over the fistula at the end of dialysis). At the time of the next dialysis, the catheter is pushed though the thrombus (similar in effect to how a blunt needle traverses the clot when the buttonhole technique is being used).

An embodiment of the invention may include two funnel shaped or cylindrical shaped vascular access chambers as described herein that may be incorporated into one body, oriented in opposite directions in order to enable blood inflow and outflow into a vessel during hemodialysis treatment. The vascular access device may include a tapered cylindrical cavity whose relative angle with the blood vessel changes gradually from a greater angle at the first end to a lesser angle at the second end. This may guide the entry of a flexible needle or catheter into the vascular access device while enabling delivery of blood flow through the flexible needle or catheter that is parallel to the blood vessel flow in order to further reduce turbulence and vessel wall damage.

In an embodiment of the invention, the vascular access device may accept a catheter that passes through a needle inserted in the vascular access device. The catheter may be radiopaque, and the catheter may be advanced with radiologic control until its tip is in a central venous position. This catheter can be used for dialysis and provide a safer means of catheter dialysis during the maturation period of an AV fistula or a prosthetic graft.

The vascular access device may decrease the maturation time required for a fistula by providing a protected access into the vessel and avoiding damage to the initially thin wall of the vein before its maturation.

The vascular access device may further be affixed to a high flow vein such as the axillary vein either as a single unit or as a tandem unit containing two conical or cylindrical shaped chambers oriented in opposite directions in the same device and allow immediate and permanent chronic use for dialysis patients or chemotherapy patients. This may eliminate the need to create and maintain AV fistulas as well as the need for permanent dialysis catheters, reducing the U.S. health care budget by over $2 billion per year in expenses.

BRIEF DESCRIPTION OF THE DRAWINGS

The present invention is described in detail below with reference to the attached Figures, wherein.

DETAILED DESCRIPTION OF EMBODIMENTS OF THE INVENTION

Figure 1:
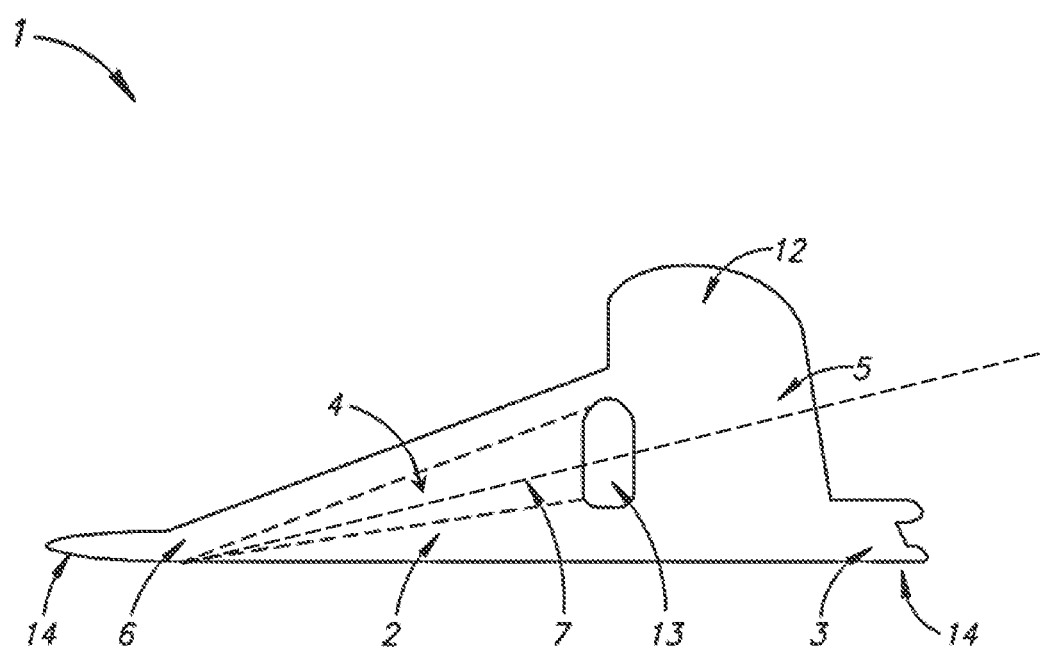
FIG. 1 depicts a schematic and illustrative side view of a vascular access device in an embodiment of the invention.

Various embodiments of the invention are discussed in detail below. While specific embodiments are discussed, specific terminology is employed for the sake of clarity. However, the invention is not intended to be limited to the specific terminology so selected and it should be understood that this is done for illustration purposes only. A person of ordinary skill in the art will recognize that other components and configurations can be used without departing from the spirit and scope of the invention. Each specific element includes all technical equivalents that operate in a similar manner to accomplish a similar purpose.

In the following description of some embodiments of the invention, directional words such as, for example, "top," "bottom," "left," "right," "upward" and "downward," are employed by way of description and not limitation with respect to the orientation of the device and its various components as illustrated in the drawings.

Figure 12:
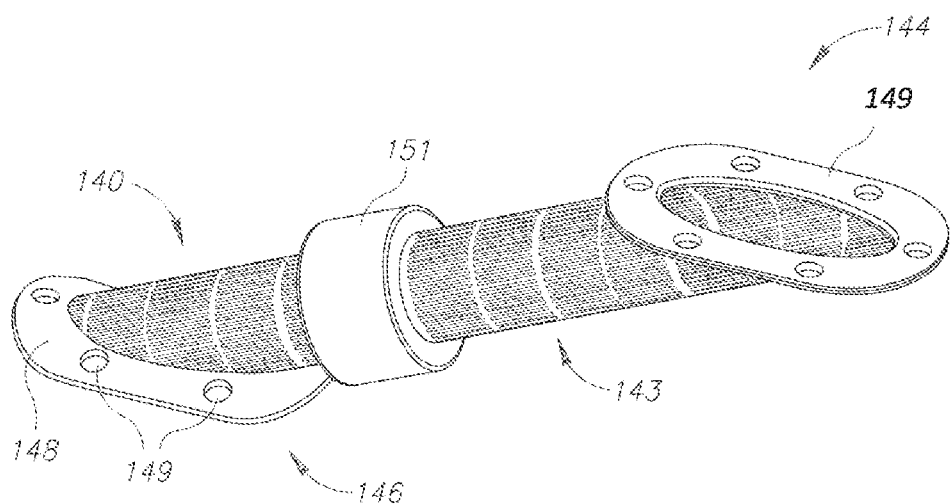
FIG. 12 depicts an embodiment of the invention including a porous cylindrical structure.
Figure 15:
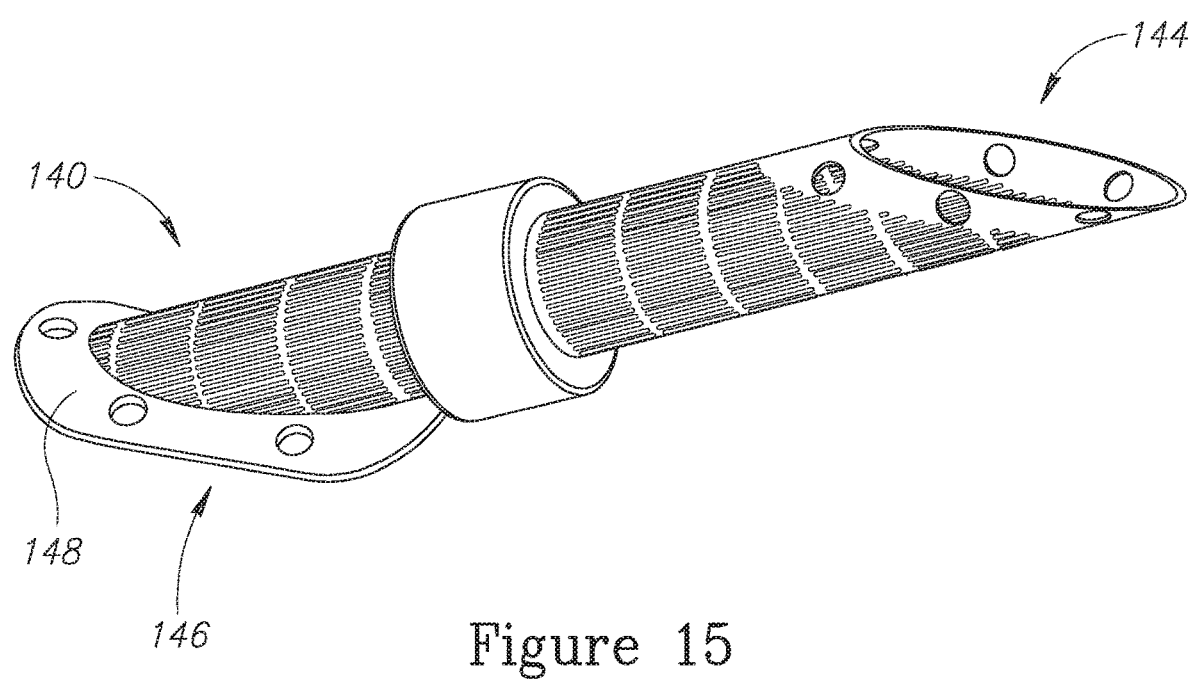
FIG. 15 depicts a cylindrical vascular access device according to an alternative embodiment of the invention.

FIG. 12 depicts a cylindrical tube 140 having a first opening at a first end 144 and a second opening at a second end 146 according to one embodiment. The first end 144 is adapted to receive a needle penetrating through a patient's skin so that the needle is directed to the same location on a blood vessel for repeated access to a blood vessel, for dialysis or other condition requiring repeated vascular access. The second end 146 is provided with a footplate 148 adapted for attachment to the blood vessel, For this purpose, suturing holes 149 may be provided. The second end 146 is formed at an angle with respect to the longitudinal axis of the cylindrical conduit, so that cylinder 140 is deployed at an angle with respect to the blood vessel after the device has been installed. The resulting entry angle of the needle may be in a range of 5 degrees to 45 degrees, preferably 5 degrees up to 30 degrees. Footplate 148 is provided around the periphery of the opening, on the second end. The first end 144 may be adapted for attachment to a dermal layer with second footplate 147, similar to first footplate 148. In an embodiment shown in FIG. 15, the first end is not provided with a footplate, but may be cut or provided with a predetermined length so that it may be positioned just below the skin in the area of needle insertion.

The device may be deployed using an open surgical technique where an incision is made in proximity to a blood vessel and the tube is sutured to the outside wall of the blood vessel on one end and to or in the dermis layer of the skin on the second end.

Alternatively, the tube may be deployed using a minimally invasive, percutaneous technique similar to the current deployment of a stent in a blood vessel. Access to the blood vessel will be achieved by placing a needle into the vessel, followed by advancement of a guide wire into the vessel, followed by introduction of a foraminous tube that is attached to the outside of the vessel using a balloon to deploy the tube with a fixation mechanism that may include a combination of hooks and bioglue to fix the tube to the outside wall of the vessel, preventing blood from leaking from the vessel into surrounding tissues. Deployment may include other techniques used to deploy endovascular devices.

The surface of the tube may be continuous, i.e., without holes, and made of a bioabsorbable material. Alternatively, in the embodiment shown, tube 140 is a bioabsorbable or biocompatible metal or polymer and has a plurality of through holes 143 arranged in a pattern on the surface of the tube to promote tissue ingrowth. For this purpose, the through holes have a size 30 to 300 μm in at least one dimension, preferably 50 to 200 μm, and the area of the holes may comprise 30-90 percent of the surface area, and in embodiments 30-70 percent. In this context, "surface area" means the outer wall of the tube.

Figure 13:
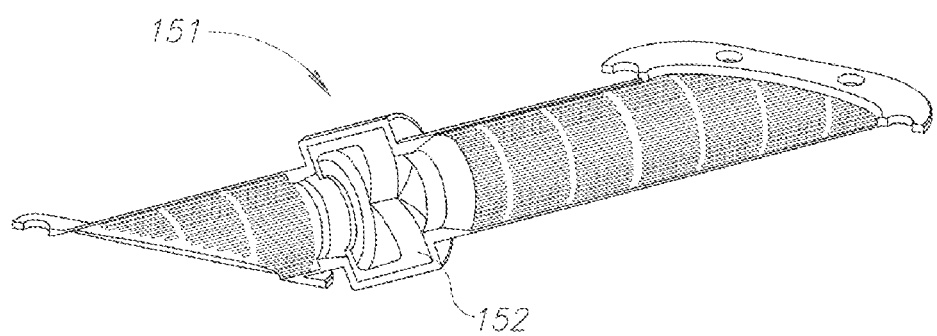
FIG. 13 depicts a cross sectional view of the vascular access device depicted in FIG. 12.

As seen best in the cutaway view of FIG. 13, one-way valve 151 made of a flexible material 152 prevents back flow of blood from the vessel when the needle is inserted.

Figure 14:
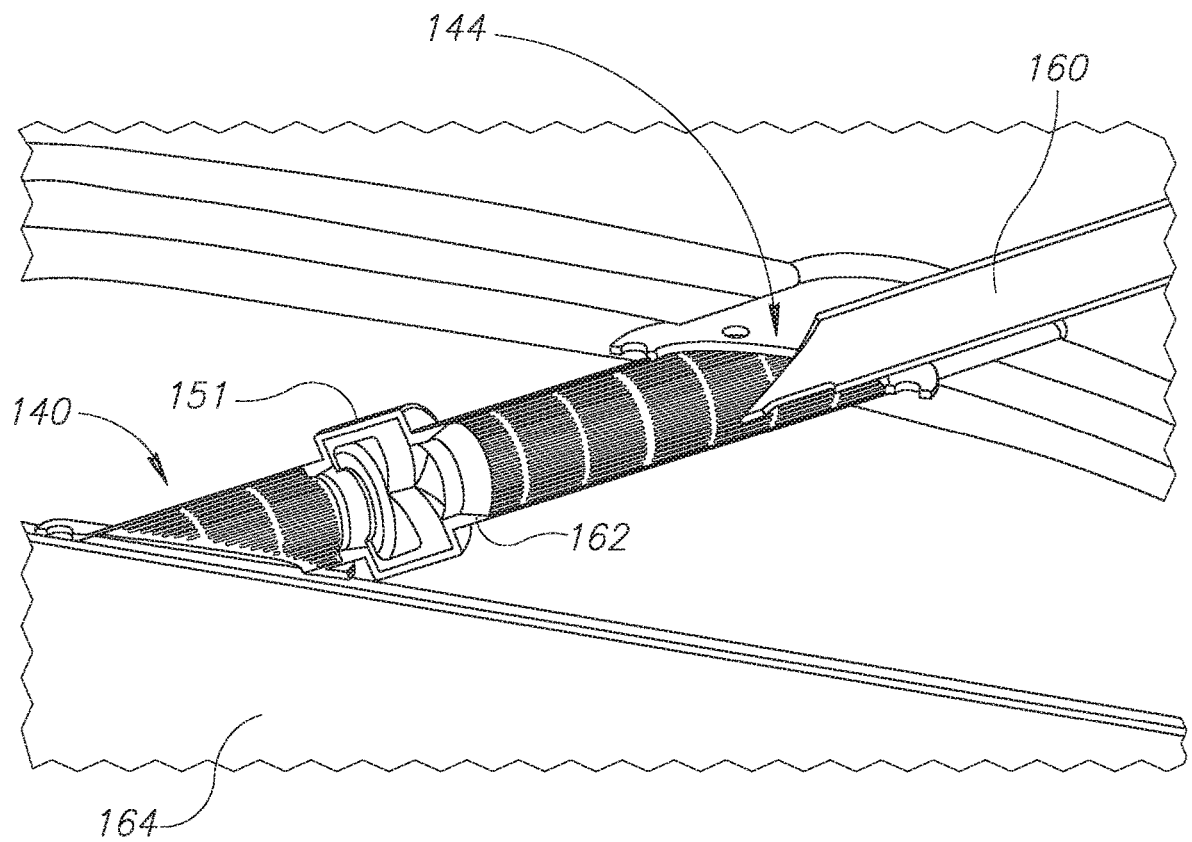
FIG. 14 is a cross sectional view of a cylindrical vascular access device according to an embodiment of the invention installed in the subcutaneous space.
Figure 16:
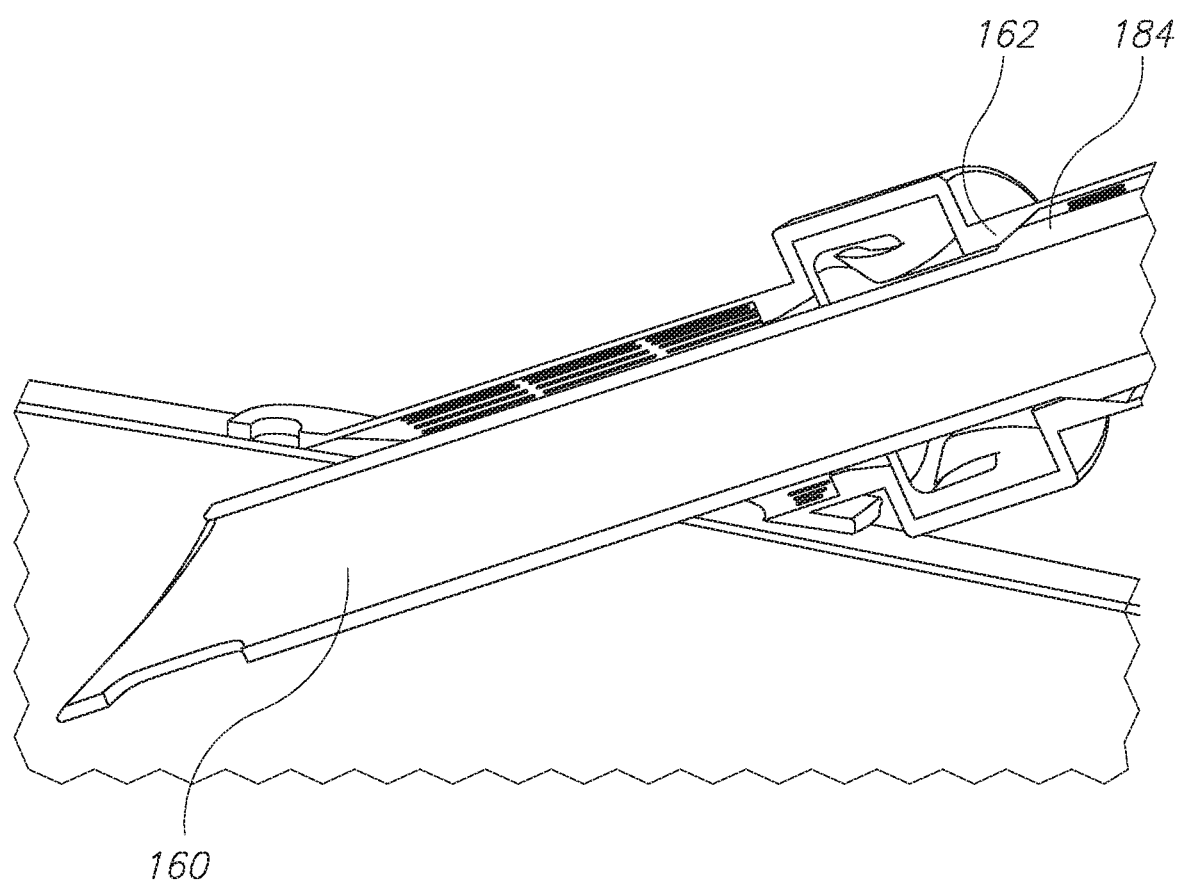
FIG. 16 depicts a cylindrical vascular access device with a needle stop according to an embodiment of the invention.

The cross sectional view of FIG. 14 shows needle 160 penetrating the skin and entering the first opening 144 in the first end of tube 140. The device generally may be adapted for use with 13-20 gage needles. On the side of valve 151 away from blood vessel 164, a needle stop 162 is provided to prevent penetration of the back wall of vessel 164. Operation of stop 162 is shown in FIG. 16, wherein a needle is provided having a wide portion 184 for engaging stop 162. The wide portion may be a feature of the needle itself, or a sleeve or ring that slides over the needle to provide an element to engage stop 162.

As seen in several views, the vascular access device has a stent like structure, except that unlike an arterial stent, the device according to the invention is affixed in the subcutaneous space. Through holes 143 may serve to promote tissue growth into the lattice-like walls of the device and affix the device in the subcutaneous space.

Figure 10:
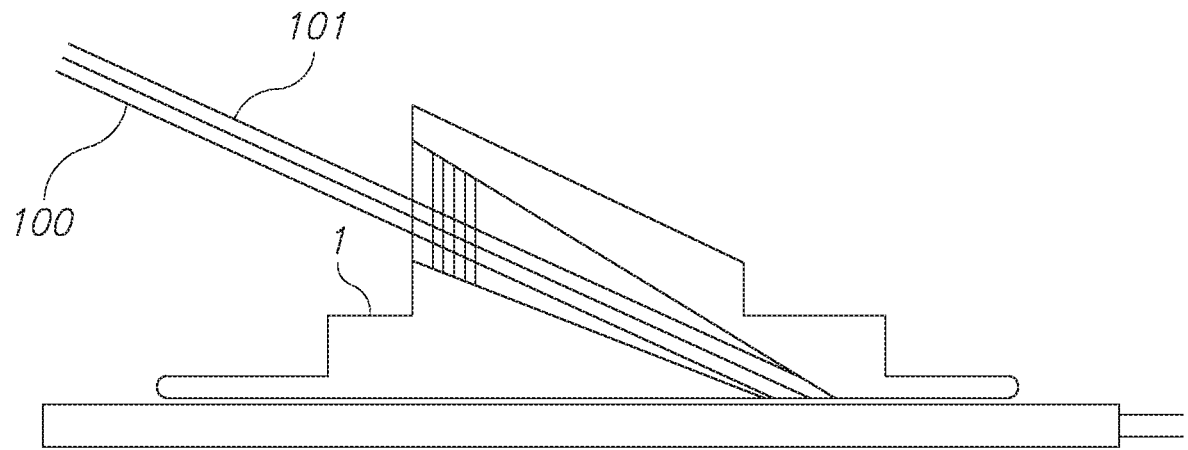
FIG. 10 depicts a further embodiment of the invention including a catheter.

FIG. 1 depicts a schematic and illustrative side view of a vascular access device 1 according to an embodiment of the invention. The vascular access device 1 may be a part or portion of a vascular access kit including further a needle assembly to facilitate easier access to a vascular system by, for example, unskilled or untrained persons. The vascular access device 1 may be used to guide a needle from the skin into an opening in a vessel. In an embodiment of the invention, the vascular access device 1 will guide a needle from the skin into the vessel at the exact same opening in the vessel each time. In an embodiment of the invention, the needle may be a flexible needle. In another embodiment of the invention, the vascular access device 1 may be used with a catheter. As shown in FIG. 10, catheter 100 may be passed through a needle 101 in the vascular access device 1. A "vessel", as used herein, includes any conduit that blood flows in, for example, by way of non-limiting example, a native AV fistula, an AV fistula synthetic graft, a vein, or an artery.

The vascular access device 1 may include a main body 2 with a first end 5 below the skin and a second end 6 that is contiguous with a vessel. The main body 2 may be formed of a biocompatible matelial such as, by way of non-limiting example, silicone, polymers, or metals (e.g. titanium). The main body 2 may comprise an inner surface that defines a funnel, or a cone-shaped tapered interior cavity or it may be a cylinder shape, 4 extending between openings at a first end 5 and a second end 6 along an oblique axis 7. The tapered inner surface 30 may be defined by, for example, but not limited to, silicone, polymers, or metals (e.g. titanium). The inner surface 4 in the main body 2 may be configured to guide a dialysis access needle from the first end 5 toward an opening at the second end 6. In an embodiment of the invention, the opening at the first end 5 may be broad, and the opening at the second end 6 may be narrow. In an embodiment of the invention, the second end 6 may be large enough to allow passage of a cannula to permit the vascular access device 1 to provide easy access into the vessel to treat complications, such as, by way of non-limiting example, lumen stenosis that may lead to fistula failure, in the lumen of the vessel.

A user may direct the access needle to the first end 5 of the vascular access device 1 that is located subcutaneously, and the cone-shaped tapered interior cavity, 4 guides the needle to the second end 6 that opens into the vessel. As a consequence, the needle is guided to puncture the vessel at a specific and repetitive location on the vessel wall. When the vascular access device 1 is implanted (i.e. secured to the wall of a vessel), the access needle may be received at the wall of the vessel at an angle a parallel to the vessel. In an embodiment of the invention, the angle parallel to the vessel is 5 to 45 degrees towards arterial flow or in line with venous flow. In a preferred embodiment, the angle a parallel to the vessel is 5 to 30 degrees towards arterial flow or in line with venous flow. In yet another preferred embodiment, the angle a parallel to the vessel is 10 to 30 degrees towards arterial flow or in line with venous flow. The angle a parallel to the vessel enables a more laminar flow, in turn, contributing to less turbulence within the vessel. The decreased turbulence may decrease red cell damage (hemolysis) and damage to the vessel wall.

In an embodiment of the invention, the first end 5 may comprise a septum (not pictured) to serve as a self-sealing hemostatic barrier. In an embodiment of the invention, the vascular access device 1 may comprise a fluid-sealed central cavity that comprises an anticoagulant, such as, by way of non-limiting example, heparinized saline, to prevent blood clots inside the cavity. In an embodiment of the invention, a one-way valve (not pictured), such as, by way of non-limiting example, a duck-billed shaped valve, may be attached to the second end 6 of the main body 2 to prevent back bleeding into the cone-shaped tapered interior cavity 4. In an embodiment of the invention, the vascular access device 1 may comprise a palpable protuberance 2 on the superficial surface of first end 5 that can be palpated through the skin. The palpable protuberance 12 may be of 2-3 millimeters in size. The palpable protuberance 12 may allow a user to feel and envision the position of the target entry membrane, the first end 5, located right below the palpable protuberance 12.

In an embodiment of the invention, the footplate 3 of the main body 2 is bonded to the vessel using, for example, but not limited to, a bioglue material avoiding obstruction to the distal puncture site where the dialysis access needle enters the vessel., while the vascular access device 1 is implanted. In another embodiment of the invention, the footplate 3 of the main body 2 is bonded to the vessel using, for example, but not limited to, a porous mesh material, to encourage ingrowth of fibrous tissue from the vessel, further securing the vascular access device 1 to the vessel. In yet another embodiment of the invention, the vascular access device 1 may comprise one or more apertures 14 on the fore and aft sides of the footplate 3 to affix the vascular access device to a vessel using sutures. In another embodiment of the invention, the vascular access device 1 may comprise one or more additional wings 13 containing apertures on either side of the superior aspect of the main body 2 which contain holes to enable suture fixation of the vascular access device 1 to the surrounding subcutaneous tissue. These one or more wings may prevent rotation of the vascular access device 1 on the vessel. In an embodiment of the invention, the vascular access device 1 comprises both one or more aperture(s) 14 and one or more wing(s) 13. In yet another embodiment of the invention, the vascular access device 1 comprises use of one or more of the synthetic mesh material, bioglue, one or more apertures 14 and/or one or more wings 13 to affix the vascular access device 1 to the vessel and/or surrounding tissue.

In an embodiment of the invention, the vascular access device 1 may be enabled to be used prior to the fistula maturation. Generally, a bridging dialysis catheter must be placed to allow a fistula to 6-8 weeks to mature. In an embodiment of the invention, the vascular access device 1 may be immediately implanted on a newly constructed fistula contiguous to the wall of the vessel through a small arc of the circumference of the vessel. In yet another embodiment of the invention, the distal second side 6 may be large enough to allow a dialysis access needle to be placed into the vessel to allow threading of a catheter through the dialysis access needle into a vessel which may include advancement into a location in the e central venous system to allow for immediate dialysis. In an embodiment of the invention, the catheter may be removed upon maturation of the fistula. In an embodiment of the invention, the vascular access device 1 may be used to access the mature fistula.

Figure 2:
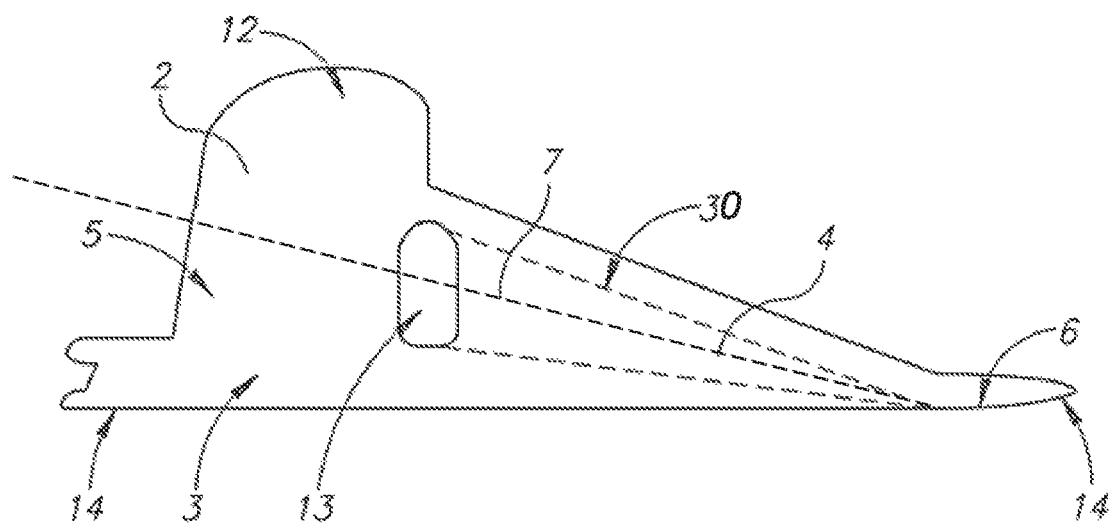
FIG. 2 depicts an opposite side view of a vascular access device, in an embodiment of the invention.
Figure 3:
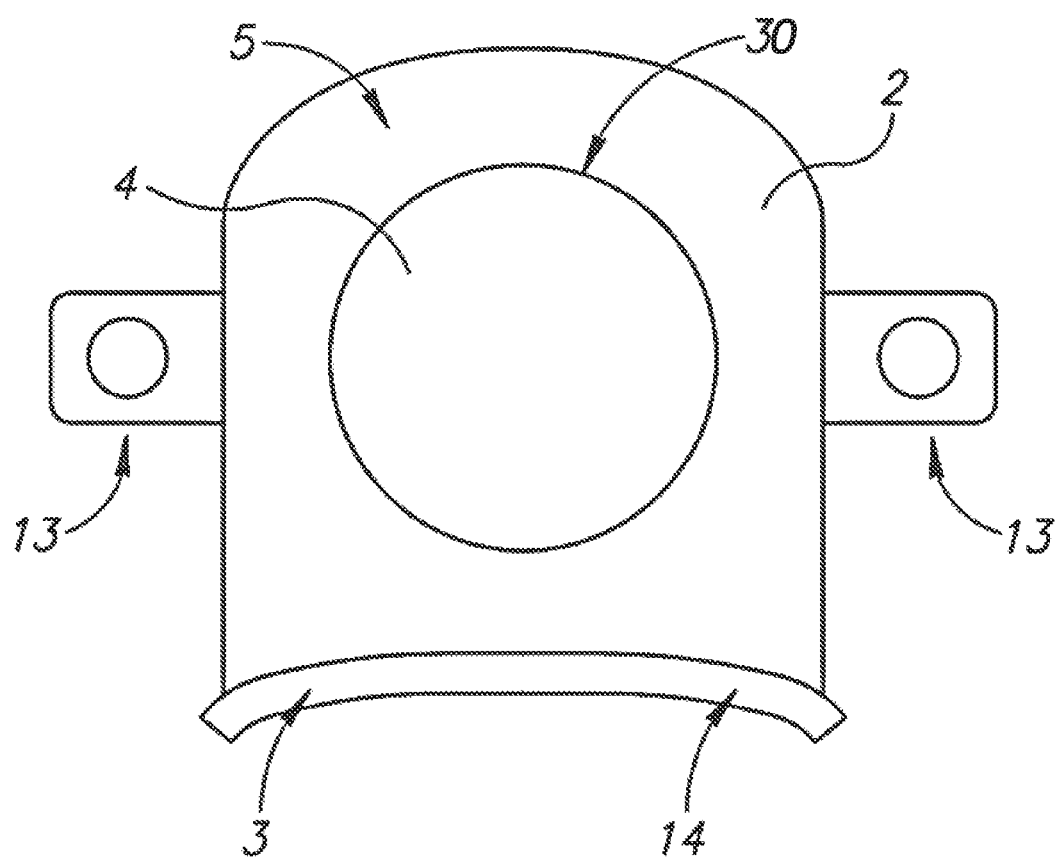
FIG. 3 depicts a schematic and illustrative view of a vascular access device from the vessel side, in an embodiment of the invention.
Figure 4:
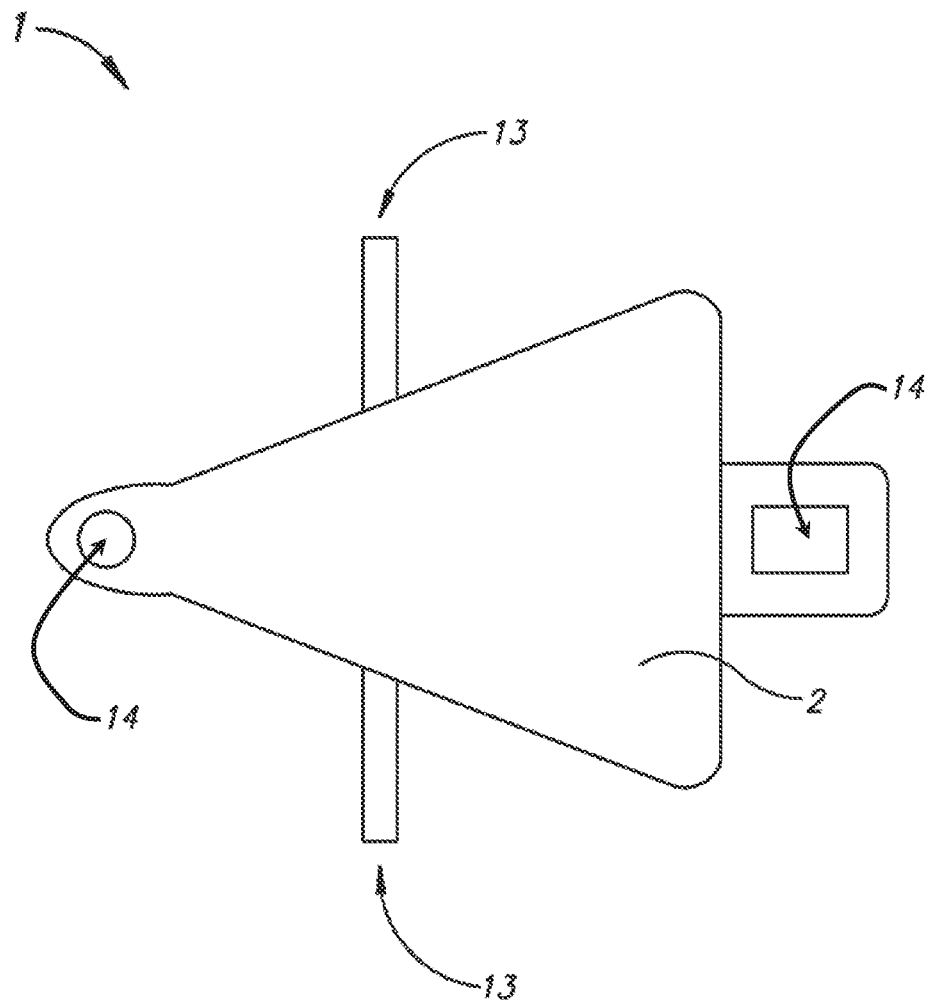
FIG. 4 depicts a schematic and illustrative top view of a vascular access device, in an embodiment of the invention.

FIG. 2 depicts a schematic and illustrative side view of a vascular access device 1, associated with the description of FIG. 1. FIG. 3 depicts a schematic and illustrative view of a vascular access device 1 from the vessel, associated with the description of FIG. 1. FIG. 4 depicts a schematic and illustrative proximal view of a vascular access device 1, associated with the description of FIG. 1.

Figure 5:
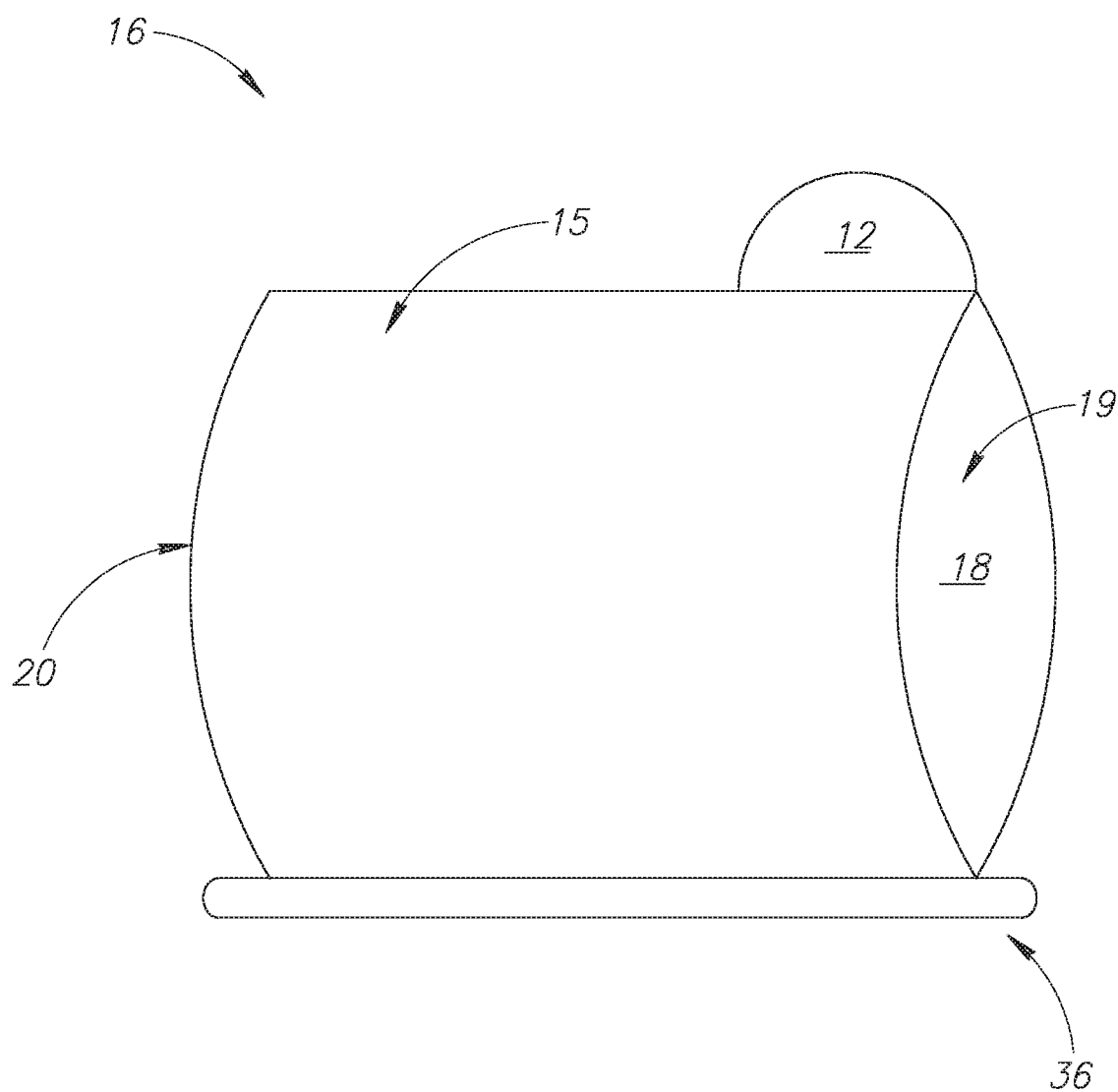
FIG. 5 depicts a schematic and illustrative side view of a vascular access device according to an embodiment of the invention.

FIG. 5 depicts a schematic and illustrative side view of a vascular access device 16 according to an embodiment of the invention. The vascular access device 16 may be a part of a vascular access kit including a needle assembly to facilitate easier access to a vascular system by, for example, persons of lower level skills. The vascular access device 16 may comprise a cylinder 15 of biodegradable or stem cell type matrix, which may form a cylindrical cavity from the skin level to the vessel. In an embodiment of the invention, the cylinder 15 may be implanted at the dermis of the skin. An inner surface of the cylinder 15 may define a funnel, or a cone-shaped tapered interior cavity, 18 extending between openings at a first end 19 and a second end 20. The inner surface may be defined by, for example, a funnel shaped receptacle for the initial part of the cylinder 15, made of a biodegradable or stem cell type matrix, to guide the needle from the skin puncture site into the cylinder 15. In an embodiment of the invention, the access needle may be guided by the inner surface toward a point in the wall of the vessel at an angle a parallel to the vessel. In an embodiment of the invention, the angle a parallel to the vessel is 5 to 45 degrees towards arterial flow or in line with venous flow. In a preferred embodiment, the angle a parallel to the vessel is 5 to 30 degrees towards arterial flow or in line with venous flow. In yet another preferred embodiment, the angle a parallel to the vessel is 10 to 30 degrees towards arterial flow or in line with venous flow. The angle a parallel to the vessel enables a more laminar flow, in turn, contributing to less turbulence within the vessel. The decreased turbulence may decrease red cell damage (hemolysis) and damage to the vessel wall. In an embodiment of the invention, the cylinder 15 is parallel to the vessel.

In an embodiment of the invention, the vascular access device 16 may comprise a palpable protuberance 12 on the superficial surface of first end 19 that can be palpated through the skin. The palpable protuberance 12 may allow a user to feel and envision the position of the target entry membrane, the first end 19, located right below the palpable protuberance 12.

In another embodiment of the invention, the vascular access device 16 may comprise one or more wings containing apertures on either side of the superior aspect of the cylinder 15 which contain holes to enable suture fixation of the vascular access device 16 to the surrounding subcutaneous tissue. These one or more wings may prevent rotation of the vascular access device 16 on the vessel. In yet another embodiment of the invention, the second end 20 may comprise a biodegradable footplate 36 with flanges at 90 degree angles to one another to permit suturing the footplate 36 to the vessel wall. In yet another embodiment, the cylinder 15 may be bonded to a biodegradable footplate 36 with synthetic mesh to permit fixing the cylinder 15 to the vessel wall by ingrowth of tissue from the vessel. The vascular access device 16 may be considered in reference to previous embodiments as described herein.

Figure 6:
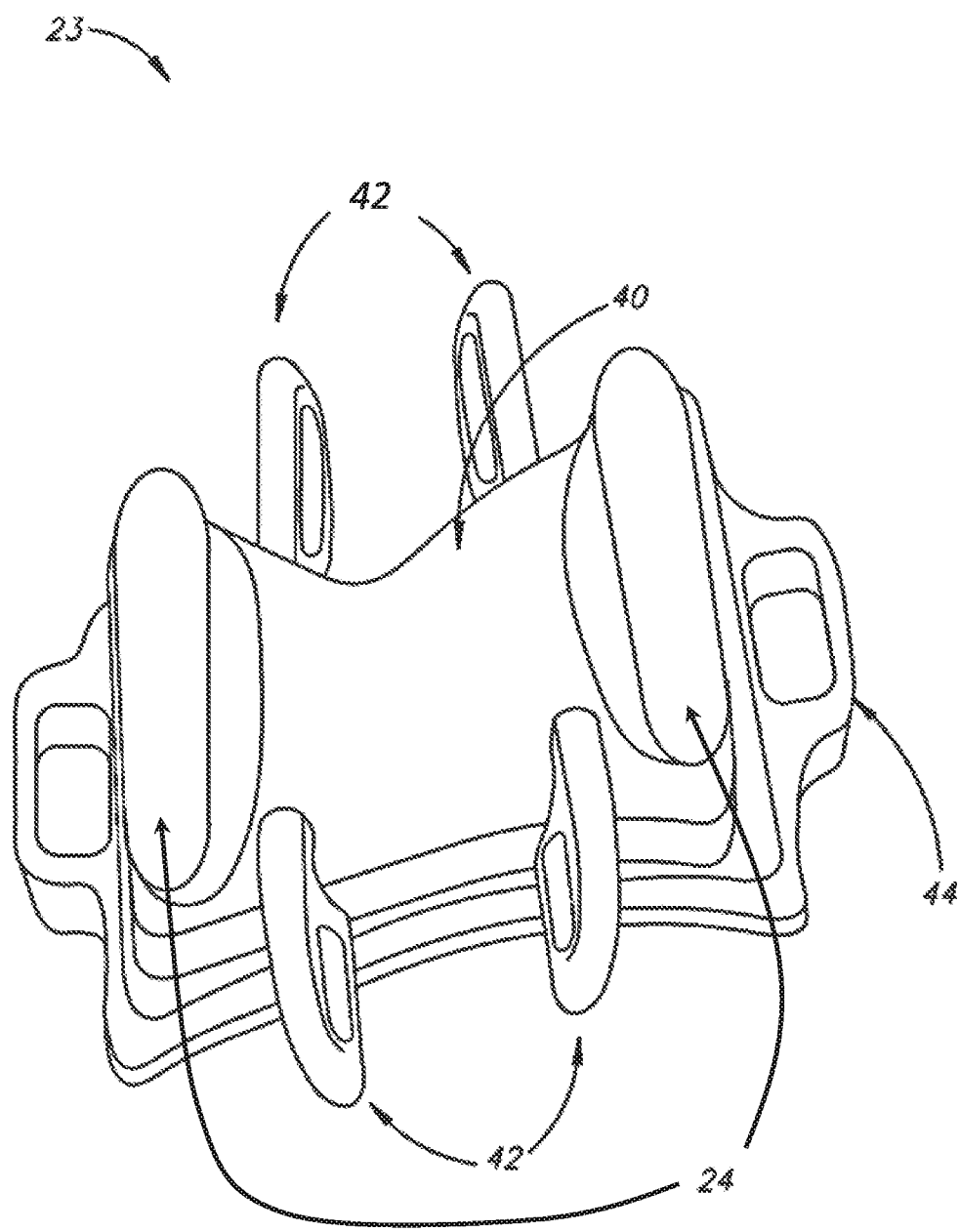
FIG. 6 depicts a schematic and illustrative view of a vascular access device according to an embodiment of the invention having inflow and outflow conduits.

FIG. 6 depicts a schematic and illustrative view of a vascular access device 23 according to an embodiment of the invention. In an embodiment of the invention, the vascular access device 23 comprises one main body 40 with two parallel cone-shaped chambers 24 oriented in opposite direction to enable inflow and outflow into a vessel during hemodialysis treatment. The two dialysis access needles enter the vessel at least 3 centimeters apart. In an embodiment of the invention, two dialysis access needles enter the vessel at least 3 centimeters apart to avoid admixture of blood that may result in ineffective dialysis.

The vascular access device 23 may comprise one or more wings 42 containing apertures on either side of the superior aspect of the vascular access device 23 which contain holes to enable suture fixation of the vascular access device 23 to the surrounding subcutaneous tissue. These one or more wings 42 may prevent rotation of the vascular access device 23 on the vessel. The vascular access device 23 may comprise a biodegradable footplate 44 with flanges to permit suturing the footplate 44 to the vessel wall. In yet another embodiment, the vascular access device 23 may be bonded to a biodegradable footplate 44 with synthetic mesh to permit fixing the vascular access device 23 to the vessel wall by ingrowth of tissue from the vessel. The vascular access device 23 may be considered in reference to previous embodiments as described herein.

Figure 7:
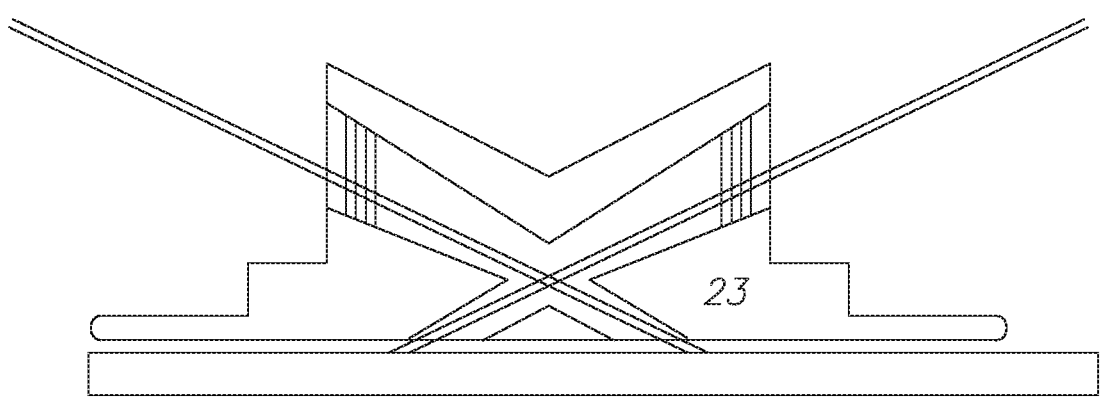
FIG. 7 depicts a schematic and illustrative cross sectional view of a vascular access device having inflow and outflow conduits according to an embodiment of the invention.

FIG. 7 depicts a schematic and illustrative cross-sectional view of a vascular access device 23, associated with the description of FIG. 6, showing a second tube in a main body of the device.

Figure 8:
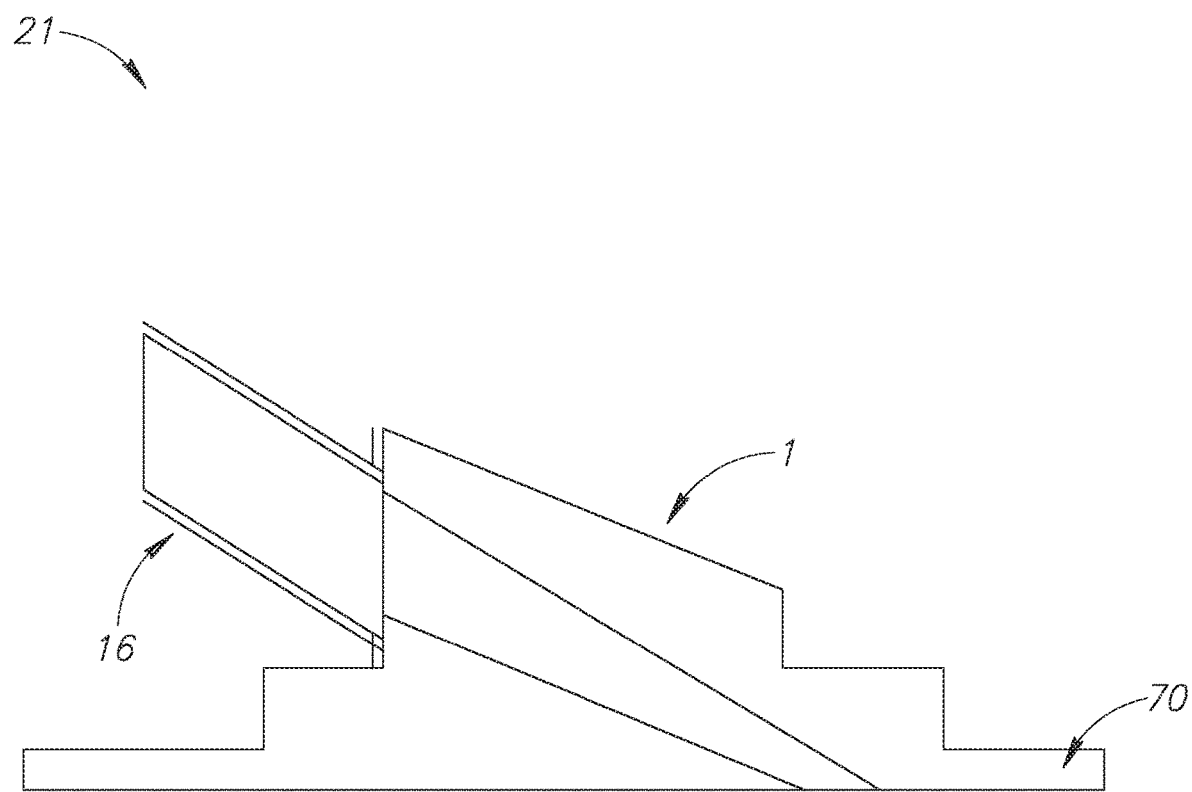
FIG. 8 depicts a schematic and illustrative view of a vascular access device according to an embodiment of the invention, having a cylindrical conduit.

FIG. 8 depicts a schematic and illustrative side view of a vascular access device 21 according to an embodiment of the invention. In an embodiment of the invention, the vascular access device 21 comprises a distal end of a vascular access device 16 bonded to a vascular access device 1. The vascular access device 21 may comprise one or more apertures on the fore and aft sides of a footplate 70 to affix the vascular access device to a vessel using sutures. In another embodiment of the invention, the vascular access device 21 may comprise one or more wings containing apertures on either side of the superior aspect of the vascular access device 21 which contain holes to enable suture fixation of the vascular access device 21 to the surrounding subcutaneous tissue. These one or more wings may prevent rotation of the vascular access device 21 on the vessel. In an embodiment of the invention, the vascular access device 21 comprises both one or more aperture(s) and/or one or more wing(s). The vascular access device 21 may be considered in reference to previous embodiments as described herein.

Figure 9:
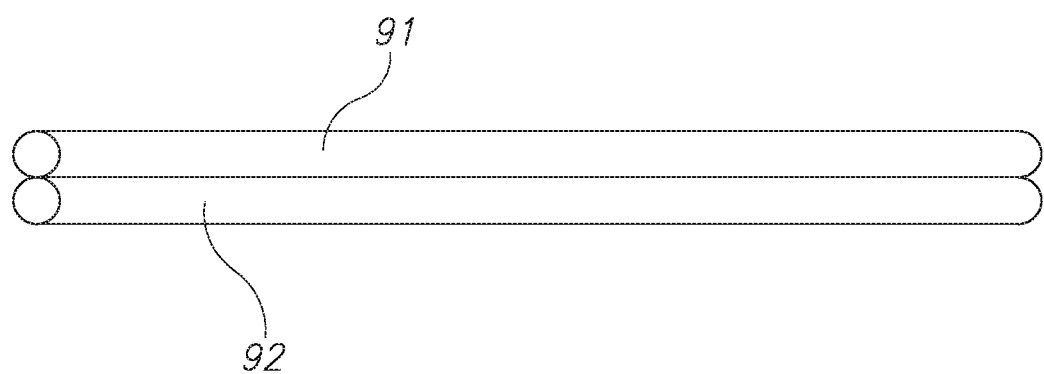
FIG. 9 depicts a schematic and illustrative view of a needle with two lumens as used with a vascular access device according to an embodiment of the invention.

FIG. 9 depicts a schematic and illustrative view of a needle with two lumens 91, 92 to be used with a vascular access device as described herein. In an embodiment of the invention, an operator may pierce the skin with a specifically designed needle with two lumens vascular access device. The needle with two lumens may comprise a locking device that slides to fix the needle entering a vascular access device described herein in relation to the entry point of the needle through the skin. In an embodiment of the invention, at the end of a procedure, the "needle with two lumens" may allow the needle to be withdrawn into a vascular access device described herein to flush an inner cavity described herein using heparinized saline delivered through the smaller bore channel and suctioned out of the chamber using the larger bore tube. In embodiments of the invention, one or more needles may have one or more diameters. In an embodiment of the invention, two adjacent needles may be bonded together. The vascular access device may be considered in reference to previous embodiments as described herein.

Figure 11:
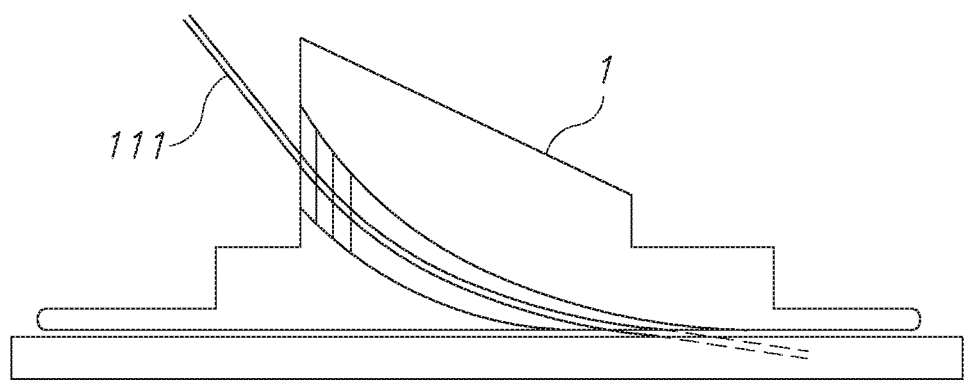
FIG. 11 depicts a further embodiment of the invention including a flexible needle.

In an embodiment of the invention, a vascular access device comprises a main body whose design includes an orifice that is attached on a blood vessel and designates an exact and narrow location where a needle enters the vessel. The orifice may be a part of the main body's surface that is attached to the vessel wall, wherein the surface is designed to protect the vessel wall and is fixed to the vessel and surrounding tissue by sutures and/or by a mesh that may facilitate tissue growth around the surface. The interior design of the main body may guide a needle to enter the orifice at an exact and narrow range of entry angles relative to the blood vessel, wherein the entry angle is selected to reduce flow disturbances within the blood vessel. The main body may be designed to accept a rigid needle at angles that vary by not more than 20 degrees from the entry angle to the orifice, and the main body may guide the needle to a desired entry angle at the orifice. In embodiments, such as shown in FIG. 11, the interior configuration of the main body 1 may be designed to accept a flexible needle 111 or a catheter at angles that vary by not more than 45 degrees from the entry angle to the orifice, and the main body may guide the needle to a desired entry angle at the orifice. The entry angle may reduce the risk of vessel's back-wall perforation. The main body may have an internal chamber that has two sealed openings that a needle can penetrate, the first below the skin and the second close to the orifice. In embodiments of the invention, the vessel may be considered in reference to previous embodiments as described herein. In embodiments of the invention, the entry angle is less than 45 degrees. In embodiments of the invention, the entry angle is between 5 and 30 degrees. In embodiments of the invention, the entry angle changes gradually from approximately 30 degrees at the opening below the skin to approximately 5 degrees at the orifice. The vascular access device may be considered in reference to previous embodiments as described herein.

If a device becomes infected, it can be removed and placed at a distant location on the same fistula. The fistula may be repaired with a vein patch angioplasty.

If a patient has no suitable upper extremity veins, the procedure can be performed on lower extremity vein sites, or an AV fistula graft can be placed in the upper extremity with attachment of the vascular access device to the graft.

An advantage of the vascular access device may include, for example, but is not limited to, immediate access after creation of the fistula (similar to current dialysis catheter access techniques) prior to maturation. The reservoir may allow short, wide bore access to the fistula using short 14 gauge access needles that allow much higher flow rates than standard dialysis catheters markedly reducing duration of dialysis sessions. The vascular access device may decrease the maturation time required for a fistula by providing a protected access into the vessel and avoiding damage to the initially thin wall of the vein before its maturation.

In embodiments of the invention, the vascular access device may accept a catheter that passes through a needle inserted in the vascular access device. The catheter may or may not be radiopaque, and may be advanced with or without radiologic control until its tip is in a central venous position. This catheter can be used for dialysis and provide a safer means of catheter dialysis during the maturation period of the AV fistula or a prosthetic graft. If the access ports become infected, or are otherwise rendered dysfunctional, they can be removed and replaced in a different location on the native fistula with repair of the fistula using, for example, a vein patch angioplasty technique or a vein interposition graft. The vascular access device may facilitate the performance of endovascular interventions to treat complications within the fistula such as intimal hypertrophy and stenosis.

In embodiments of the invention, the vascular access device may eliminate backflow into the device. The vascular access device will be easily found by a user supporting or undergoing dialysis.

In embodiments of the invention, the vascular access device, as a single device or as a tandem unit with two conical shaped chambers oriented in opposite directions in the same unit, may be affixed to a high flow vein such as the axillary vein and allow immediate and permanent chronic use for dialysis or chemotherapy. This may eliminate the need to create and maintain AV fistulas and dialysis catheters, reducing the U.S. healthcare budget by over $2 billion each year in expenses. Embodiments of the vascular access devices described herein may further include a tapered cylindrical cavity whose relative angle with the vessel changes gradually from a greater angle at the first end to a lesser angle at the second end. This may guide the entry of a flexible needle or catheter into the vascular access device while enabling delivery of blood flow through the flexible needle or catheter parallel to the vessel flow to reduce turbulence and vessel wall damage.

While various embodiments of the present invention have been described above, it should be understood that they have been presented by way of example only, and not limitation. Thus, the breadth and scope of the present invention should not be limited by any of the above-described embodiments, but should instead be defined only in accordance with the following claims and their equivalents.

What is claimed is:

1. A vascular access device for accessing a blood vessel, adapted to couple to an outer wall of the blood vessel and a dermal layer of a skin, comprising:
   a body;
   a lumen passing through the body, from a first end of the body to a second end of the body opposite said first end;
   a first opening through said first end of said body to said lumen;
   a second opening through said second end of said body to said lumen, wherein said lumen is sized and shaped to direct a tip of a dialysis needle entering said body through said first opening to exit said body through said second opening;
   a vessel interface surrounding the second opening at said second end, adapted for attachment to the outer wall of the blood vessel; and
   a skin interface surrounding the first opening at said first end, sized and shaped for direct attachment of said first end of said body to the dermal layer of the skin underneath the dermal layer of the skin; and wherein said vessel interface and said skin interface are on opposite ends of said body.

2. The vascular access device of claim 1, wherein said first opening is substantially the same size and shape as said second opening.

3. The vascular access device of claim 1, wherein said skin interface includes a suturing hole.

4. The vascular access device of claim 1, wherein a width of said lumen at said first opening is less than twice a width of said dialysis needle having a width within the range of 13 to 20 gauge.

5. The vascular access device of claim 1 wherein said skin interface includes a flange surrounding at least a portion of said first opening.

6. The vascular access device of claim 1, wherein said blood vessel interface extends outward from an edge of said second opening.

7. The vascular access device of claim 6, wherein said blood vessel interface is substantially parallel to said skin interface.

8. The vascular access device of claim 1, wherein said blood vessel interface includes a suture hole.

9. The vascular access device of claim 8, wherein said vessel interface includes a concave surface configured to fit a wall of said blood vessel.

10. The vascular access device of claim 1, wherein said skin interface is at an angle of between 5 to 45 degrees to a longitudinal axis of said lumen.

11. The vascular access device of claim 1, wherein said body is cylindrical.

12. The vascular access device according to claim 1, wherein the body has a plurality of through holes between an outer surface of the body and said lumen, each of said through holes having a size in a range of 30 μm to 300 μm in at least one dimension.

13. The vascular access device according to claim 12, wherein an area of the through holes encompasses 30 to 90 percent of the outer surface of the body.

14. The vascular access device according to claim 1, wherein the body is formed of a bioabsorbable material.

15. The vascular access device according to claim 1, further comprising: a valve between the first end and the second end; said valve having a movable member allowing fluid flow in only one direction.

16. The device according to claim 1, further comprising:
a needle stop, adapted to engage a portion of a needle inserted into the lumen and stop forward movement of the needle before the needle reaches a back wall of the blood vessel.

17. The vascular access device of claim 1, wherein said device, including said lumen and said skin interface, are configured to be implanted wholly below the skin.

18. A vascular access system, comprising the vascular access device of claim 1, and a catheter received in the lumen, the catheter adapted to be guided by an inner surface of the lumen toward and into the blood vessel.

19. A method of providing access to a blood vessel utilizing an under skin access device including a body and a lumen passing through the body from a first opening at a first end of the body to a second opening at a second end of the body opposite said first end, the first end of the body including a skin interface surrounding the first opening and the second end of the body including a vessel interface surrounding the second opening, comprising:
attaching the vessel interface to an outer wall of the blood vessel; and
directly attaching the skin interface to a dermal layer of a skin underneath the dermal layer of the skin of a subject.

20. The method of claim 19, wherein said directly attaching includes suturing.

21. The method of claim 19, wherein said attaching the vessel interface includes suturing.

22. The method of claim 19, further wherein said directly attaching includes fixating the first end to the skin of the subject such that a longitudinal axis of the lumen is arranged at an angle between 5 and 45 degrees relative to the skin.

23. The method of claim 19, further comprising:
encouraging ingrowth of tissue into said lumen by supplying a plurality of through holes between an outer surface of the body and said lumen, each of said through holes having a size in a range of 30 μm to 300 μm in at least one dimension.

24. The method of claim 19, further comprising:
repeatedly inserting a tip of a dialysis needle by puncturing the skin of the subject, through said lumen to said outer wall of said blood vessel, and through said outer wall into said blood vessel.

25. The method of claim 24, wherein said repeatedly inserting is into a same location on the blood vessel every time.

26. The method of claim 19, further comprising:
preventing back bleeding by encouraging ingrowth of tissue into said lumen by supplying a plurality of through holes between an outer surface of the body and said lumen.

* * * * *